United States Patent [19]

Fravolini

[11] Patent Number: 4,535,079

[45] Date of Patent: Aug. 13, 1985

[54] ALKANOLAMINOXY DERIVATIVES OF 3,4-DIHYDRO-2H-1,4-BENZOTHIAZIN-3-ONE, THEIR PRODUCTION PROCESS, AND THEIR PHARMACEUTICAL USE

[75] Inventor: Arnaldo Fravolini, S.Sisto, Italy

[73] Assignee: Mediolanum Farmaceutici S.R.L., Milan, Italy

[21] Appl. No.: 543,013

[22] Filed: Oct. 18, 1983

[30] Foreign Application Priority Data

Oct. 20, 1982 [IT] Italy ............................... 49313 A/82

[51] Int. Cl.$^3$ ..................... A61K 31/38; C07D 279/10
[52] U.S. Cl. ........................................ 514/225; 544/52
[58] Field of Search ........................... 544/52; 424/246

[56] References Cited

U.S. PATENT DOCUMENTS 3,337,628  8/1967  Crowther et al. ............... 260/570.7

FOREIGN PATENT DOCUMENTS 2912445 10/1980 Fed. Rep. of Germany ........ 544/52
1373537 10/1971 United Kingdom .................. 544/52
1549945  8/1979 United Kingdom .................. 544/52

OTHER PUBLICATIONS

Troxler, Merck Index, Ninth ed., 1976, Merck and Co., N.J., p. 968, 7240.
Morrison et al., Morrison and Boyd Textbook of Organic Chemistry, Allyn and Bacon, 1978, pp. 767–769.
Chemical Abstracts, vol. 95, No. 13, Sep. 28, 1981, p. 711, No. 115577x, Columbus, Ohio, US & JP A 8151465 (Yoshitomi Pharmaceutical Industries, Ltd.), 09/05/1981, *Abstract.
Chemical Abstracts, vol. 97, No. 3, Jul. 19, 1982, p. 712, No. 23776z, Columbus, Ohio, US & JP-A8221377 (Shionogi and Co., Ltd.), 04-02-1982, *Abstract.
Journal of the Chemical Society, c, vol. 15, 1971, pp. 2696–2699, R. T. Coutts et al., "Acetylation and acetoxylation of 4-hydroxy-1,4-benzothiazin- and -benzoxazin-3(4H)-ones (cyclic hydroxamic acids)", *p. 2696, formula I, p. 2697, formula IIIf*.

*Primary Examiner*—Henry R. Jiles
*Assistant Examiner*—J. G. Mullins
*Attorney, Agent, or Firm*—Stevens, Davis, Miller & Mosher

[57] ABSTRACT

Object of the invention is a class of new organic compounds derived from 1,4-benzothiazine through substitution of an hydrogen atom in position 6, 7 or 8 by an oxypropanolammine radical monosubstituted in N and furthermore a series of new phenyl derivatives of 1,4-benzothiazine, obtained as intermediate in the synthesis of oxypropanolammine derivatives, and process for obtained the new compounds in form suitable for the preparation of pharmaceutical compositions having antihypertensive, vasodilating and antiarrhythmic activity.

6 Claims, No Drawings

ALKANOLAMINOXY DERIVATIVES OF 3,4-DIHYDRO-2H-1,4-BENZOTHIAZIN-3-ONE, THEIR PRODUCTION PROCESS, AND THEIR PHARMACEUTICAL USE

This invention relates to alkanolaminoxy derivatives of 3,4-dihydro-2H-1,4-benzothiazin-3-one, their production process, and the intermediate products obtained during the course of the process.

The invention also relates to new pharmaceutical agents having beta-blocking activity and various grades of cardio-selectivity which are useful in the treatment of cardiovascular malfunctions such as cardiac arrhythmia and arterial hypertension, and to the pharmaceutical compounds which contain them.

In the present state of the art, certain organic compounds containing a side chain derived from propanol, such as propranolol, are known to exert a particular pharmacodynamic action characterised by the blocking of the beta neuroreceptors. It is also known that in these compounds, the remainder of the molecule can assume structures which are very different from each other, and each of which can influence the other characteristics of the drug, such as the various aspects of its toxicity, the pharmacokinetic and the manifestation of side-effects, both positive (cardioselectivity, sympaticomimethic intrinsic activity, vasolidating activity), and negative.

According to the present invention, new compounds have now been discovered which manifest beta-blocking activity to a surprising degree, in additon to antiarrhythmic and antihypertensive activity, while possessing low toxicity. The compounds of the present invention active in this manner correspond to the following general structure:

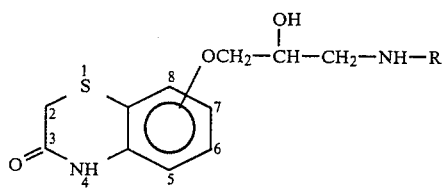

in which R represents an isopropyl, secondary butyl, tertiary butyl or 2(3,4-dimethoxy-phenyl)-ethyl radical. Said compounds are obtained by reacting an amino-3,4-dihydro-2H-1,4-benzothiazin-3-one (in which the amino group is in position 6, 7 or 8 in the molecule) with sodium nitrite, and decomposing the diazo compound thus obtained, through the Sandmeyer reaction leading to the formation of new derivatives characterised by the structure of hydroxy-3,4-dihydro-2H-1,4-benzothiazin-3-ones (in which the hydroxyl group is correspondingly in position 6, 7 or 8 in the molecule). These compounds are then reacted with α-epichlorohydrin to give the respective 2,3-epoxy derivatives, which are then reacted with the suitably substituted aliphatic amine, to give the respective alkanolaminoxy derivatives, which constitute the final products according to the present invention.

The invention also relates to new compounds obtained as intermediates in the aforesaid process, namely 6-, 7- or 8-hydroxy-3,4-dihydro-2H-1,4-benzothiazin-3-one, and 6-, 7- or 8-(2,3-epoxy)-propoxy-3,4-dihydro-2H-1,4-benzothiazin-3-one.

The reaction scheme for obtaining the compounds according to the invention is illustrated hereinafter, its significance being quite clear to any expert of the art in that it is based on the application of currently used chemical reactions:

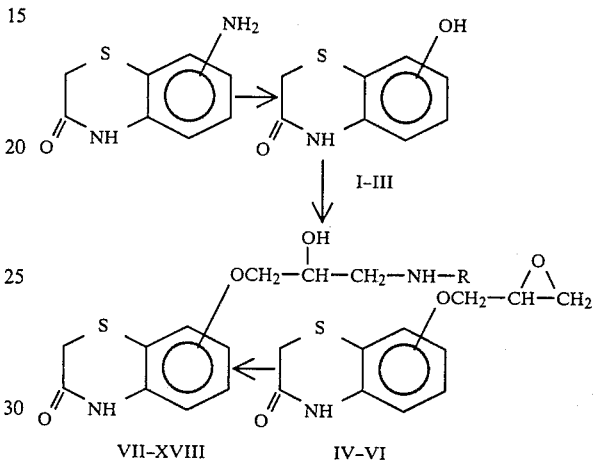

The characteristics of the three new intermediate phenolic compounds and the three new intermediate epoxy compounds are given in Table 1.

The characteristics of the fifteen new propanolamino compounds, which possess the aforesaid pharmacological activity, and are described in greater detail hereinafter, are given in Table 2, in which the formula is shown as the oxalate and fumarate.

TABLE 1

| Compound | Substituent | M.P. °C. | cryst. solv. | formula |
|---|---|---|---|---|
| I | 6-OH | 218–221 | EtOAc | $C_8H_7NO_2S$ |
| II | 7-OH | 250–153 | EtOAc | $C_8H_7NO_2S$ |
| III | 8-OH | 188–190 | EtOH | $C_8H_7NO_2S$ |
| IV | 6-OCH$_2$—CH—CH$_2$ (epoxy) | 153–155 | EtOH | $C_{11}H_{11}NO_3S$ |
| V | 7-OCH$_2$—CH—CH$_2$ (epoxy) | 198–201 | EtOH | $C_{11}H_{11}NO_3S$ |
| VI | 8-OCH$_2$—CH—CH$_2$ (epoxy) | 192–193 | EtOH | $C_{11}H_{11}NO_3S$ |

TABLE 2

| Compound | Posit. | R | M.P. °C. | cryst. solv. | |
|---|---|---|---|---|---|
| VII | 6 | iso-C$_3$H$_7$ | 202–204 | EtOH | $C_{14}H_{20}N_2O_3S \cdot C_4H_4O_4$ |
| VIII | 6 | iso-C$_4$H$_9$ | 185–188 | EtOH/acetone | $C_{15}H_{22}N_2O_3S \cdot C_4H_4O_4$ |
| IX | 6 | tert-C$_4$H$_9$ | 242–244 | iso-PrOH | $C_{15}H_{22}N_2O_3S \cdot C_4H_4O_4$ |
| X | 6 | sec-C$_4$H$_9$ | 228–230 | EtOH | $C_{15}H_{22}N_2O_3S \cdot C_4H_4O_4$ |
| XI | 7 | iso-C$_3$H$_7$ | 217–220 | EtOH | $C_{14}H_{20}N_2O_3S \cdot C_2H_2O_4$ |
| XII | 7 | iso-C$_4$H$_9$ | 208–210 | EtOH | $C_{15}H_{22}N_2O_3S \cdot C_2H_2O_4$ |
| XIII | 7 | tert-C$_4$H$_9$ | 251–254 | EtOH | $C_{15}H_{22}N_2O_3S \cdot C_2H_2O_4$ |

TABLE 2-continued

| Compound | Posit. | R | M.P. °C. | cryst. solv. | |
|---|---|---|---|---|---|
| XIV | 7 | sec-$C_4H_9$ | 211–213 | EtOH | $C_{15}H_{22}N_2O_3S.C_2H_2O_4$ |
| XV | 8 | iso-$C_3H_7$ | 234–237 | EtOH | $C_{14}H_{20}N_2O_3S.C_4H_4O_4$ |
| XVI | 8 | iso-$C_4H_9$ | 234–236 | EtOH | $C_{15}H_{22}N_2O_3S.C_4H_4O_4$ |
| XVII | 8 | tert-$C_4H_9$ | 288–289 | iso-PrOH | $C_{15}H_{22}N_2O_3S.C_4H_4O_4$ |
| XVIII | 8 | sec-$C_4H_9$ | 218–221 | EtOH | $C_{15}H_{22}N_2O_3S.C_4H_4O_4$ |
| XIX | 6 | (MeO)$_2$PhEt | 192–193 | EtOH | $C_{21}H_{26}H_2O_5S.C_4H_4O_4$ |
| XX | 7 | (MeO)$_2$PhEt | 162–165 | MeOH/EtOAc | $C_{21}H_{26}N_2O_5S.C_4H_4O_4$ |
| XXI | 8 | (MeO)$_2$PhEt | 206–208 | MeOH | $C_{21}H_{26}N_2O_5S.C_4H_4O_4$ |

Detailed non-limiting examples of the typical preparation of the intermediate and final products are given hereinafter to illustrate the present invention.

EXAMPLE 1

Preparation of 7-hydroxy-3,4-dihydro-2H-1,4-benzothiazin-3-one (Compound II)

60 ml of acetic acid are added to a suspension of 9 g (0.05 moles) of 7-amino-3,4-dihydro-2H-1,4-benzothiazin-3-one (see A. Martani, A. Fravolini, G. Grandolini, Ann. Chim. (Rome), 58, 1226; 1958) in 50 ml of water. 200 ml of 20% $H_2SO_4$ are added to the solution obtained, leading to the precipitation of the amine sulphate.

A solution of 4.5 g (0.065 moles) of $NaNO_2$ (dissolved in the minimum quantity of water) is added dropwise to this suspension, which is maintained between 0° and 5° C. A clear solution is obtained when the addition is complete. The reaction mixture is left to stand for 1 hour at ambient temperature, and is then treated with urea on the tip of a spatula in order to destroy the excess nitrite. 50 ml of 20% $H_2SO_4$ are added, and the reaction mixture is raised to 70° C. and kept at this temperature until $N_2$ ceases to be evolved. After cooling, the solution is extracted several times with ethyl acetate. The ester extracts are added together, and washed several times with water, then dried over $Na_2SO_4$, the solvent finally being removed by evaporation under reduced pressure. A residue is obtained constituting product II in the crude state. After crystallizing from ethyl acetate, it has a melting point of 250°–253° C.

EXAMPLE 2

Preparation of 7-(2,3-epoxy)-propoxy-3,4-dihydro-2H-1,4-benzothiazin-3-one (Compound V)

1.65 g (0.009 moles) of compound II obtained in the preceding example are added to a solution of 0.5 g (0.012 moles) of NaOH dissolved in 15 ml of water, after which 9.2 g of α-epichlorohydrin are slowly added under agitation. The reaction mixture is kept under agitation for 24 hours, after which the precipitated product is collected (1.3 g) and washed with water.

The epoxide V obtained in this manner is purified by chromatography in a silica gel column, eluting with chloroformcyclohexane 8:2. After this purification, the product obtained weighs 0.6 g and has an M.P. of 198°–201° C.

EXAMPLE 3

Preparation of 7-(3-tert.butylamino-2-hydroxy)-propoxy-3,4-dihydro-2H-1,4-benzothiazin-3-one (Compound XIII)

A mixture of 1 g of compound V obtained in the preceding example and 40 ml of ethanol is suspended in an autoclave, and an excess of tert.butylamine (15 ml) is added. The reaction is carried out in the autoclave at 120° C. for 5 hours. After this period, the reaction mixture is evaporated to dryness under reduced pressure, the residue then taken up in a little ethanol, and the amine precipitated by adding hexane. The precipitated amine is collected and crystallized from a cyclohexane-ethyl acetate mixture, to give a product having a melting point of 98°–100° C. 0.5 g of the crystallized amine are dissolved in acetone, and a solution of acetone saturated with oxalic acid is dripped into this solution. The product XIII which precipitates as the oxalate is collected and crystallized from ethanol. Melting point of the oxalate: 251°–254° C.

EXAMPLE 4

Preparation of 8-(2,3 epoxy)-propoxy-3,4-dihydro-2H-1,4-benzothiazin-3-one (Compound VI) of formula:

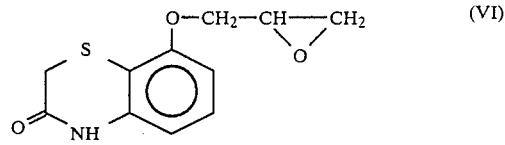

To a solution of 2 g of compound of formula III in 15 ml $H_2O$, containing 0.6 g of NaOH, epichlorohydrin is added in large excess (10.9 g), dissolved in methanol. The reaction mixture is kept under agitation for 24 hours at room temperature. Then the mixture is concentrated through evaporation and thereafter poured into water and extracted with ethyl-acetate. The obtained solution is dried with $Na_2SO_4$ and then evaporated A solid reddish residue (g 2,4) is obtained. The thus obtained epoxide is purified by chromatography in a silica gel column, eluting with a mixture chloroform/cyclohexane 1:1 and then with mixture 4:1. The pure epoxide is obtained in the eluate. The epoxide, crystallized from ethanol, has melting point of 192°–193° C.

PHARMACOLOGICAL DESCRIPTION

In vitro experimental study

The beta-blocking activity and the antiarrhythmic activity were determined in vitro.

(a) Beta-blocking activity: isolated guinea pig atrium method

The compounds under examination were tested on the isolated guinea pig atrium for their capacity to antagonise the positive inotropic and chronotropic effects induced by isoprenaline. The preparations were made up from native guinea pigs weighing 450±50 g and suspended in a 10 ml bath of oxygenated Tyrode maintained at 29° C., the frequency and force of contraction being recorded by means of an isotonic pen loaded with 1.5 g and having an amplification ratio of 1:15. The substance under test was added to the medium in a volume of 0.1 ml 10 minutes before stimulation by isoprenalina administered at the optimum concentration which had been determined on the basis of the reactivity of the preparation. The results are shown in Table 3, expressed as $IC_{25}$ (concentration able to inhibit by 25% the response to stimulation by isoprenaline), in comparison with carteolol, i.e. 5-(3-tert.butylamino-2-hydroxypropoxy)-3,4-dihydro-carbostyryl-hydrochloride.

TABLE 3

Beta-blocking activity: antagonism in the response of the isolated guinea pig atrium to isoprenaline; concentration inhibiting 25% of this response ($IC_{25}$).

| COMPOUND | POSITIVE INOTROPIC EFFECT WITH ISOPRENALINE $IC_{25}$ (g/ml) | POSITIVE CHRONOTROPIC EFFECT WITH ISOPRENALINE $IC_{25}$ (g/ml) |
| --- | --- | --- |
| VII | $3.46 \times 10^{-7}$ | $4.15 \times 10^{-7}$ |
| VIII | $7.41 \times 10^{-7}$ | $8.61 \times 10^{-7}$ |
| IX | $2.03 \times 10^{-7}$ | $2.55 \times 10^{-7}$ |
| X | $6.70 \times 10^{-7}$ | $8.03 \times 10^{-7}$ |
| XI | $7.43 \times 10^{-8}$ | $9.10 \times 10^{-8}$ |
| XII | $3.61 \times 10^{-7}$ | $5.50 \times 10^{-7}$ |
| XIII | $5.65 \times 10^{-8}$ | $7.03 \times 10^{-8}$ |
| XIV | $9.78 \times 10^{-8}$ | $2.02 \times 10^{-7}$ |
| XV | $5.87 \times 10^{-8}$ | $6.41 \times 10^{-8}$ |
| XVI | $9.95 \times 10^{-8}$ | $1.30 \times 10^{-7}$ |
| XVII | $2.76 \times 10^{-10}$ | $9.92 \times 10^{-10}$ |
| XVIII | $7.05 \times 10^{-8}$ | $8.03 \times 10^{-7}$ |
| Carteolol* | $1.73 \times 10^{-9}$ | $9.05 \times 10^{-9}$ |

*5-(3-tert.butylamino-2-hydroxypropoxy)-3,4-dihydrocarbostyrylhydrochloride.

All the compounds of the series proved to be significantly active as blocking agents of the beta-adrenergic cardiac receptors.

(b) Beta-blocking activity by the isolated guinea pig trachea method

The series was also tested for beta-blocking activity at the level of the isolated guinea pig trachea, evaluated as antagonism to the effect of isoprenaline.

A trachea segment was withdrawn from animals weighing 450±50 g, and a spiral of tissue was prepared and then suspended in a 20 ml bath of oxygenated Tyrode containing $10^{-7}$ g/ml of acetylcholine and 10 g/ml of eserine, the bath being temperature-controlled at 37° C. The recording was made by means of an isotonic pen with maximum amplification, loaded to 0.5 g and constantly cibrated.

Having determined the sub-maximum concentration of isoprenaline for stimulating the preparation, the test substance was placed in contact with it at different concentrations 12 minutes before stimulation, then evaluating the antagonistic effect. The $IC_{50}$, i.e. the concentration able to inhibit 50% of the response to isoprenaline, was then calculated. These results are shown in Table 4.

TABLE 4

Beta-blocking activity as antagonism in the response of the isolated guinea pig trachea to isoprenaline; concentration able to inhibit 50% of the response ($IC_{50}$)

| COMPOUND | $IC_{50}$ (g/ml) |
| --- | --- |
| VII | $4.30 \times 10^{-7}$ |
| VIII | $1.14 \times 10^{-6}$ |
| IX | $5.68 \times 10^{-7}$ |
| X | $6.60 \times 10^{-7}$ |
| XI | $7.60 \times 10^{-7}$ |
| XII | $8.06 \times 10^{-7}$ |
| XIII | $1.25 \times 10^{-7}$ |
| XIV | $2.50 \times 10^{-7}$ |
| XV | $1.23 \times 10^{-7}$ |
| XVI | $1.12 \times 10^{-7}$ |

TABLE 4-continued

Beta-blocking activity as antagonism in the response of the isolated guinea pig trachea to isoprenaline; concentration able to inhibit 50% of the response ($IC_{50}$)

| COMPOUND | $IC_{50}$ (g/ml) |
| --- | --- |
| XVII | $1.50 \times 10^{-9}$ |
| XVIII | $1.21 \times 10^{-6}$ |

(c) In vitro antiarrhytmic activity—fibrillation by aconitine in the guinea pig heart perfused by the Langendorff method An interesting inhibiting effect on fibrillation induced by aconitine in the guinea pig heart perfused by the Langendorff method was determined for the compounds of the series. Oxygenated Locke-Ringer solution was used as the perfusion liquid, the temperature being maintained at 37° C. and the average perfusion pressure at 40 cm $H_2O$. Fibrillation was induced by injecting a 0.3% solution of aconitine in 20% gum arabic into the pulminary conus zone, and placing at the injection point a disc of unisized paper soaked in the same solution. The fibrillating heart frequency was between 450 and 600 beats/minute. After two minutes from the appearance of fibrillation, perfusion of the products under examination was started in scalar concentrations on a factor of 3 from $10^{-6}$ g/ml to $10^{-3}$ g/ml through the aorta, with the perfuser regulated at a rate of 1 ml/minute, and continued for 30 minutes. The minimum concentration was then determined at which the substances under examination were able to reverse the occurring fibrillation within the 30 minutes from the commencement of perfusion.

TABLE 5

Antiarrhythmic activity: minimum tested concentration which reverses the fibrillating effect of aconitine on the guinea pig heart perfused by the Langendorff method.

| COMPOUND | CONCENTRATION g/ml |
| --- | --- |
| VII | $1 \times 10^{-5}$ |
| VIII | $1 \times 10^{-4}$ |
| IX | $3 \times 10^{-5}$ |
| X | $1 \times 10^{-4}$ |
| XI | $3 \times 10^{-6}$ |
| XII | $3 \times 10^{-5}$ |
| XIII | $3 \times 10^{-6}$ |
| XIV | $1 \times 10^{-5}$ |
| XV | $1 \times 10^{-6}$ |
| XVI | $3 \times 10^{-6}$ |
| XVII | $3 \times 10^{-7}$ |

TABLE 5-continued

Antiarrhythmic activity: minimum tested concentration which reverses the fibrillating effect of aconitine on the guinea pig heart perfused by the Langendorff method.

| COMPOUND | CONCENTRATION g/ml |
|---|---|
| XVIII | $1 \times 10^{-6}$ |
| Propranolol | $3 \times 10^{-6}$ |

IN VIVO EXPERIMENTAL STUDY

Protection from the methal effect of aconitine in the guinea pig. For the compounds according to the invention, an evaluation was made of their capacity to antagonise the lethal effect of aconitine in native guinea pigs of both sexes having an average weight of $400\pm50$ g, anesthetized with 10% ethylurethan (1 g/kg i.p.), by making an E.C.G. precardiacal recording. Death was induced by perfusing aconitine through the jugular at a dose of 150 γ/kg/hour (5 ml/hour). The time of commencement of arrhythmia, the time of commencement of fibrillation and the time of death were checked. The product under examination were administered to the jugular vein 10 minutes before commencement of perfusion in doses from 0.01 mg/kg to 10 mg/kg. Table 6 shows the results as a percentage increase in the time of death by aconitine with respect to the control animals.

TABLE 6

Death induced by aconitine in the guinea pig: protection expressed as percentage increase, in the time of death with respect to the control animals. Intravenous administration.

| COMPOUND | DOSE μg/kg | % |
|---|---|---|
| VII | 25 | 24.1 |
| VIII | 20 | 19.0 |
| IX | 10 | 25.9 |
| X | 25 | 11.3 |
| XI | 15 | 21.3 |
| XII | 20 | 16.4 |
| XIII | 10 | 39.7 |
| XIV | 15 | 20.6 |
| XV | 9 | 48.6 |
| XVI | 10 | 32.2 |
| XVII | 9 | 55.4 |
| XVIII | 10 | 49.2 |

Table 7 shows the $LD_{50}$ values for the male Wistar rat by intravenous administration.

TABLE 7

| COMPOUND | $LD_{50}$ RAT, I.V. mg/kg |
|---|---|
| VII | 80 |
| VIII | 83 |
| IX | 75 |
| X | 78 |
| XI | 65 |
| XII | 82 |
| XIII | 60 |
| XIV | 68 |
| XV | 73 |
| XVI | 67 |
| XVII | 50 |
| XVIII | 75 |

TABLE 7-continued

| COMPOUND | $LD_{50}$ RAT, I.V. mg/kg |
|---|---|
| Carteolol | 50 |

CLINICAL EXPERIMENTAL STUDY

Preliminary clinical tests on the compounds according to the invention, carried out on a group of 10 patients suffering from ventricular and supraventricular arrhythmias, showed that doses of between 0.1 and 5 mg/day administered parenterally led to a reduction in both types of arrhythmia to the extent of their returning to normal conditions. In patients with hypertension, the compounds are effective at a dosage of between 2.5 and 10 mg/day administered parenterally and between 5 and 30 mg/day administered orally. The compounds according to the present invention are therefore effective pharmaceutical agents of beta-blocking activity, for treating cardiovascular malfunctions. Said Agents can be administered parenterally in a dosage of between 0.1 and 10 mg per day, or orally in a dosage of between 5 and 30 mg per day. Said pharmaceutical agents can be made up into pharmaceutical compositions for oral or parenteral administration by adding pharmaceutically compatible excipients and carriers.

What is claimed is:

1. Alkanolaminoxy derivatives of 3,4-dihydro-2H-1,4-benzothiazin-3-one of formula

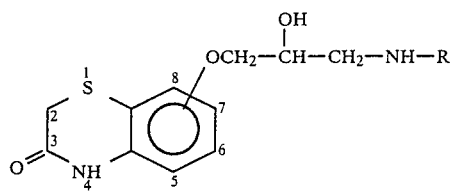

in which R is an isopropyl, secondary butyl, tertiary butyl or 2(3,4-dimethoxy-phenyl)-ethyl radical, or their salts.

2. The intermediate product 6-, 7- or 8-(2,3-epoxy)-propoxy-3,4-dihydro-2H-1,4-benzothiazin-3-one.

3. A process for preparing the compounds of the formula indicated in claim 1, characterised by reacting 6-, 7- or 8-amino-3,4-dihydro-2H-1,4-benzothiazin-3-one with sodium nitrite, subjecting the azo compound thus obtained to a Sandmeyer reaction to obtain 6-, 7- or 8-hydroxy-3,4-dihydro-2H-1,4-benzothiazin-3-one, reaction this latter compound with α-epichlorohydrin in basic aqueous solution to obtain 6- 7- or 8-(2,3-epoxy)-propoxy-3,4-dihydro-2H-1,4-benzothiazin-3-one, reacting this latter compound in alcoholic solution with an amine, $NH_2$-R, in which R has the meaning indicated in claim 1, to obtain a compound as claimed in claim 1.

4. A pharmaceutical composition having β-blocking, antiarrhythmic, vasodilating and antihypertension activity, with high cardioselectivity, comprising a β-blocking, antiarrhythmically, vasodilatingly and a hypotensively effective amount of a compound according to claim 1 and a pharmaceutically acceptable carrier.

5. A pharmaceutical composition according to claim 4, for the treatment of cardiac arrhythmias.

6. A pharmaceutical composition according to claim 4, for the treatment of arterial hypertension.

* * * * *